US006358975B1

(12) United States Patent
Eliasson et al.

(10) Patent No.: US 6,358,975 B1
(45) Date of Patent: Mar. 19, 2002

(54) METHOD OF USING SELECTIVE PARP INHIBITORS TO PREVENT OR TREAT NEUROTOXICITY

(75) Inventors: Mikael J. Eliasson; Kenji Sampei; Allen S. Mandir, all of Baltimore; Patricia D. Hurn, Upperco; Richard J. Traystman, Ruxton; Jun Bao, Baltimore; Andrew Pieper, Baltimore; Ted M. Dawson, Baltimore; Solomon Snyder, Baltimore; Valina L. Dawson, Baltimore, all of MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/502,046

(22) Filed: Feb. 11, 2000

Related U.S. Application Data

(63) Continuation of application No. PCT/US98/16959, filed on Aug. 14, 1998.
(60) Provisional application No. 60/055,866, filed on Aug. 15, 1997.

(51) Int. Cl.$^7$ .................... A61K 31/47; A61K 31/165
(52) U.S. Cl. .................... 514/309; 514/617; 514/619
(58) Field of Search ................... 514/309, 617, 514/619

(56) References Cited

U.S. PATENT DOCUMENTS

| | | | |
|---|---|---|---|
| 5,587,384 A | 12/1996 | Zhang et al. | 514/309 |
| 6,121,278 A * | 9/2000 | Jackson et al. | 514/292 |

OTHER PUBLICATIONS

Thiemermann et al., Inhibition of the activity of poly(AD-P–ribose) synthetase reduces ischemia–reperfusion injury in the heart and skeletal muscle Proc. Natl. Acad. Sci. USA (1997), 94(2), 679–683 (Copy of abstract).*

Weltin, et al., "Immunosuppressive Activities of 6(5H)–Phenanthridinone, A New Poly(ADP–Ribose)Polymerase Inhibitor", Int. J. Immunopharm., vol. 17, No. 4, 1995, pp. 265–271.

Shima, et al., "Loss of MYC gene amplified in human HL–60 cells after treatment with inhibitors of poly(ADP–ribose)polymerase or with dimethyl sulfoxide", Proc. Natl. Acad. Sci. USA, vol. 86, Oct. 1989, pp. 7442–7445.

Weltin, et al., "Effect of 6(5H)–phenanthridinone, an Inhibitor of Poly(ADP–ribose) Polymerase, on Cultured Tumor Cells", Oncology Research, vol. 6, No. 9, 1994, pp. 399–403.

Mikael J.L. Eliasson, et al., "Poly(ADP–ribose)Polymerase Gene Disruption Renders Mice Resistant to Cerebral Ischemia", Nature Medicine, vol. 3, No. 10, Oct. 1997, pp. 1089–1095.

Girish M. Shah, et al., "Complete Inhibition of Poly(ADP–ribose)Polymerase Activity Prevents the Recovery of C3H10T1/2 Cells from Oxidative Stress", Biochimica Biophysica Acta, vol. 1312, 1996, pp. 1–7.

Kazushi Takahashi, et al., "Neuroprotective Effects of Inhibiting Poly(ADP–Ribose)Synthetase on Focal Cerebral in Rats", Journal of Cerebral Blood Flow and Metabolism, vol. 17(11), 1997, pp. 1137–1142.

D. Weltin, et al., "Immunosuppressive Activities of 6(5H)–Phenanthridinone, a New Poly(ADP–Ribose)Polymerase Inhibitor", International Journal of Immunopharm, vol. 17(4), 1995, pp. 265–271.

M.J. Suto, et al., "Dihydroisoquinolinones: The Design and Synthesis of a New Series of Potent Inhibitors of Poly(ADP–ribose)Polymerase", Anti–Cancer Drug Design, vol. 6, 1991, pp. 107–117.

Denis Weltin, et al., "Effect of 6(5H)–Phenanthridinone, an Inhibitor of Poly(ADP–ribose)Polymerase, on Cultured Tumor Cells", Oncology Research, vol. 6(9), 1994, pp. 399–403.

\* cited by examiner

Primary Examiner—Kevin E. Weddington
(74) Attorney, Agent, or Firm—Banner & Witcoff, Ltd.

(57) ABSTRACT

Neutral tissue damage resulting for ischemia and reperfusion injury or neurodegenerative diseases can be prevented by administering therapeutically effective amounts of certain selective inhibitors of poly(ADP-ribose)polymerase. The inhibitors can be administered intravenously, intraperitoneally, intramuscularly, intraventricularly, or orally. They can be administered as a capsule or tablet containing single or divided dose. Alternatively, the inhibitors can be administered as a sterile solution, suspension or emulsion.

7 Claims, 6 Drawing Sheets

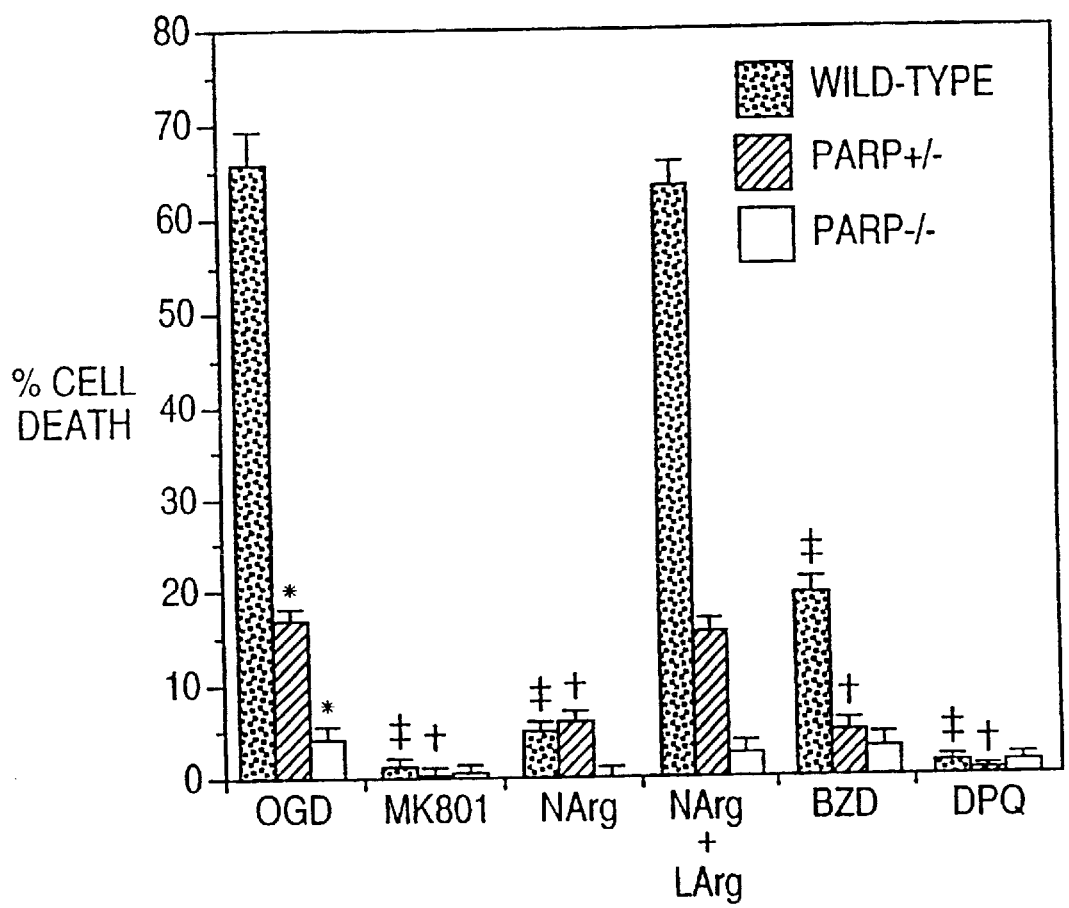

METHOD OF USING SELECTIVE PARP INHIBITORS TO PREVENT OR TREAT NEUROTOXICITY

This application is a continuation of international application No. PCT/US98/16959, filed Aug. 14, 1998, pending, which claims priority to U.S. Ser. No. 60/055,866, filed Aug. 15, 1997, now abandoned and U.S. Ser. No. 08/922,575, filed Sep. 3, 1997, now abandoned.

BACKGROUND OF THE INVENTION

1. Field of the Invention

The invention relates to the prevention and/or treatment of neural tissue damage resulting from ischemia and reperfusion injury. More particularly, the invention concerns the prevention or treatment of vascular stroke, other neurodegenerative diseases and occlusion of coronary arteries, by administering selective inhibitors of the nucleic enzyme poly(adenosine 5'-diphospho-ribose) polymerase ["poly (ADP-ribose) polymerase" or "PARP", which is also sometimes called "PARS" for poly(ADP-ribose) synthetase].

2. Description of the Prior Art

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been established, this enzyme is thought to play a role in enhancing DNA repair.

During major cellular stresses, however, the extensive activation of PARP can rapidly lead to cell death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

Neural damage following stroke and other neurodegenerative processes is thought to result from a massive release of the excitatory neurotransmitter glutamate, which acts upon the N-methyl-D-aspartate (NMDA) receptors and other subtype receptors. Evidence includes findings in many animal species, as well as in cerebral cortical cultures treated with glutamate or NMDA, that glutamate receptor antagonists block neural damage following vascular stroke. Dawson et al., "Protection of the Brain from Ischemia", *Cerebrovascular Disease*, 319–325 (ed. Batjer 1997).

The stimulation of NMDA receptors, in turn, activates the enzyme neuronal nitric oxide synthase (nNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate neurotoxicity in Primary Cortical Cultures", *Proc. Natl. Acad. Sci. USA*, 88:6368 (1991); and Dawson et al., "Mechanisms of Nitric Oxide-mediated Neurotoxicity in Primary Brain Cultures", *J. Neurosci.*, 13:2651–61 (1993). Protection against NMDA neurotoxicity can also occur in cortical cultures from mice with targeted disruption of nNOS. See Dawson et al., "Resistance to Neurotoxicity in Cortical Cultures from Neuronal Nitric Oxide Synthase Deficient Mice", *J. Neurosci.*, 16:2479–87 (1996). It is known that neural damage following vascular stroke is markedly diminished in animals treated with NOS inhibitors or in mice with nNOS gene disruption. Iadedcola, "Bright and Dark Sides or Nitric Oxide in Ischemic Brain Injury", *Trends Neurosci.*, 20:132–39 (1997); and Huang et al., "Effects of Cerebral Ischemia in Mice Deficient in Neuronal Nitric Oxide Synthase", *Science*, 265:1883–85 (1994).

FIG. 5 provides a simple model of the following sequence of the multitude of cellular events that presumably takes place in the PARP activation associated with ischemia:

(1) Ischemia following blood vessel occlusion reduces the resting membrane potential of glia and neurons in the tissue.

(2) Potassium leaks out of cells and depolarizes the neurons, leading to a massive release of glutamate.

(3) Acting via NMDA receptors, glutamate triggers a release of NO, which combines with superoxide to form peroxynitrite.

(4) Peroxynitrite damages DNA, fragments of which then activate PARP.

(5) Massive activation of PARP depletes NAD via ADP-ribose polymer formation.

(6) ATP is depleted in an effort to re-synthesize NAD, leading to cell death by energy depletion.

NO is a free radical that reacts chemically with multiple cellular targets to elicit a range of activities from cellular signalling to cell death. Most of the toxic effects of NO appear to be a result of the reaction of NO with superoxide to form the extremely toxic peroxynitrite. See Beckman et al., "Pathological Implications of Nitric Oxide, Superoxide and Peroxynitrite Formation", *Biochem. Soc. Trans.*, 21:330–34 (1993). Either NO or peroxynitrite can cause DNA damage, which activates PARP. PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-ribose) Synthetase in Neurotoxicity", *Science*, 263:786–89 (1994)) and in hippocampal slices (Wallis et al., "Neuroprotection Against Nitric Oxide Injury with Inhibitors of ADP-ribosylation, *Neuroreport*, 5:313, 245–48 (1993)). Zhang et al., U.S. Pat. No. 5,587,384 issued Dec. 24, 1996 also discusses the use of PARP inhibitors, such as benzamide and 1,5-dihydroxyisoquinoline, to prevent NMDA-mediated neurotoxicity and, thus, treat stroke, Alzheimer's disease, Parkinson's disease and Huntingtin's disease.

Using this model, the conventional thought that neurotoxicity came from glutamate acting through NO has suggested that the modest protective effects of non-selective PARP inhibitors, which are comparable to the protective effects of inhibitors of NO formation or drugs that block glutamate receptors, were the best one could reasonably expect.

The NMDA-NO model, however, provided only one potential mechanism for neural injury such as stroke. There has been substantial evidence that other mechanisms, such as the production of oxygen-free radicals, independently of nitric oxide, also play a role. For example, PARP activation has been shown to provide an index of damage following neurotoxic insults, not only by glutamate (via NMDA receptor stimulation) and reactive oxygen intermediates, but also by amyloid β-protein, n-methyl-4-phenyl-1,2,3,6-tetrahydropyridine (MPTP) and its active metabolite N-methyl-4-phenylpyridine (MPP*), which participate in such pathological conditions as stroke, Alzheimer's disease and Parkinson's disease. Zhang et al., "Poly(ADP-Ribose) Synthetase Activation: An Early Indicator of Neurotoxic DNA Damage", *J. of Neurochem.*, 65:3, 1411–14 (1995).

See also, Choi, "Glutamate Neurotoxicity and Diseases of the Nervous system, *Neuron,* 1:623–34 (1988); and Meldrum et al., "Excitatory Amino Acid Neurotoxicity and Neurodegenerative Disease", *Trends in Pharmacological Sciences,* 11:379–87 (1990); Choi et al., "The Role of Glutamate Neurotoxicity in Hypoxic ischemic Neuronal Death", *Ann. Rev. of Neurosci.,* 13:171–78 (1990). Thus, the relative contribution of oxygen-free radicals versus the NO system has been somewhat unclear.

It has been demonstrated that single injections of PARP inhibitors have reduced the infarct size caused by ischemia and reperfusion of the heart or skeletal muscle in rabbits. In these studies, a single injection of the non-selective PARP 3-aminobenzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", *Proc. Natl. Acad. Sci. USA,* 94:679–83 (1997). This finding has suggested that PARP inhibitors might be able to salvage previously ischemic heart or skeletal muscle tissue.

However, the approach of using PARP inhibitors generally to reduce NMDA-receptor stimulation or to treat or prevent tissue damage caused by NO is limited in effect. Accordingly, there remains a need for a procedure that produces a more potent and reliable effect downstream of the NMDA-NO sequence of bioevents by using an inhibitor that is selective of PARP activity itself, as opposed to using a non-selective PARP inhibitor that could exert many other non-specific actions, including depression of upstream events, such as NMDA-receptor activation and/or NO production.

The occurrence of side effects observed with non-selective PARP inhibitors are discussed in Milam et al., "Inhibitors of Poly(Adenosine Diphosphate-Ribose) Synthesis: Effect on Other Metabolic Processes," *Science,* 223:589–91 (1984). Specifically, the non-selective PARP inhibitors 3-aminobenzamide and benzamide not only inhibited the action of PARP but also were shown to affect cell viability, glucose metabolism, and DNA synthesis. Thus, it was concluded, the usefulness of these particular PARP inhibitors may be severely restricted by the difficulty of finding a dose small enough to inhibit the enzyme without producing additional metabolic effects. Banasik et al., in "Specific Inhibitors of Poly(ADP-Ribose) Synthetase and Mono(ADP-ribosyl)transferase", *J. of Biol. Chem.,* 267:1569–75 (1992), identified four compounds that were particularly good inhibitors of PARP, i.e., free of side reactions and applicable to in vivo studies. They were 4-amino-1,8-naphthalimide, 6(5H)- and 2-nitro-6(5H)-phenanthridinones and 1,5-dihydroxyisoquinoline. Comparative studies of the effects of PARP and mono(ADP-ribosyl)transferase from hen heterophils revealed high specificity of most of the potent inhibitors for PARP. Banasik et al., in "Inhibitors and Activators of ADP-ribosylation Reactions", *Molec. and Cell. Biochem.,* 138:185–97 (1994), also described a number of potent Inhibitors of PARP that are specific for PARP as opposed to mono(ADP-ribosyl) transferase.

SUMMARY OF THE INVENTION

The method of preventing neural tissue damage resulting from ischemia and reperfusion injury or neurodegenerative diseases in a mammal in accordance with the invention comprises administering to the mammal a therapeutically effective amount of a selective inhibitor of poly(ADP-ribose) polymerase (PARP). In this way, whatever biochemical mechanism or combination of mechanisms that is, in fact, responsible for the excessive PARP activation that often accompanies vascular stroke or other neurodegenerative diseases, the resulting neurotoxicity can be controlled directly and effectively.

BRIEF DESCRIPTION OF THE DRAWINGS

FIG. 2C compares the percentage of cell death when wild-type, PARP+/– and PARP–/– cells, which have been subjected to oxygen-glucose deprivation (OGD), and are then treated with MK801, nitroarginine (NArg), a combination of NArg and L-arginine (LArg), benzamide (BZD) or 3,4-dihydro-5-[4-(1-piperidinyl)-butox]-1(2H)-isoquinolinone (DPQ).

DETAILED DESCRIPTION OF THE INVENTION

Selective PARP Inhibitors

Figure 1:
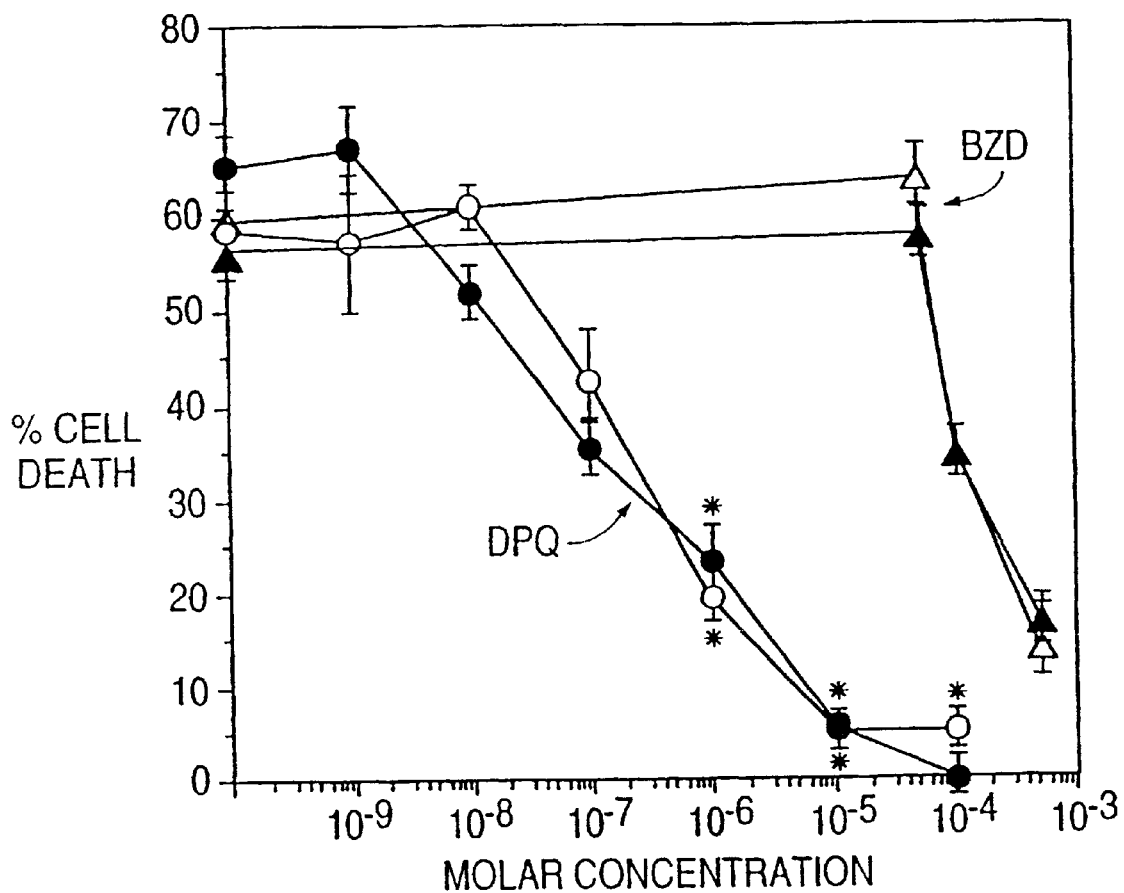
FIG. 1 shows a plot of percentage of cell death vs. molar concentration comparing the activity of the non-selective PARP inhibitor benzamide (BZD) with the specific PARP inhibitor 3,4-dihydro-5-[4-(1-piperidinyl)-butox]-1(2H)-isoquinolinone (DPQ).

What the inventors have now discovered is that PARP activation is primarily involved in neural tissue damage, including that following focal ischemia and reperfusion injury. Selective therapies designed to inhibit PARP directly and specifically can provide significant benefits in the treatment of, e.g., cerebrovascular disease or neurodegenerative diseases, as compared with therapies designed to block glutamate production, NMDA activity, NO production or NOS activity.

Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO.

As used herein, the term "neural tissue damage resulting from ischemia and reperfusion injury and neurodegenerative diseases" includes neurotoxicity, such as seen in vascular stroke and a number of neurodegenerative diseases, for example, Alzheimer's disease, Parkinson's disease and Huntingtin's disease.

As used herein, the term "selective PARP inhibitor" refers to a PARP inhibitor that has its major inhibitory effect specifically at the PARP receptor site, as opposed to blocking PARP activity by interfering with other biological pathways. Examples of such other biological pathways include NMDA-neurotoxicity or other NO-related activity that occurs biologically upstream from direct PARP activation, and also inhibitors of mono(ADP-ribosyl)transferases. It has been found that, when the PARP receptor site can be blocked selectively, a concentration sufficient to produce the desired degree of PARP inhibition can be used without incurring the risk of deleterious side effects. For example, it has been shown that non-selective PARP inhibitors such as benzamide and 3-aminobenzamide are associated with side effects involving cell viability, glucose metabolism, and DNA synthesis. Milam et al., "Inhibitors of Poly(Adenosine Diphosphate-Ribose) Synthesis: Effect on Other Metabolic Processes," *Science,* 223:589–91 (1984).

Based on cortical culture studies with PARP–/– mice [mice having a targeted disruption of the PARP gene (PARP–/–)]generated by the method of Wang et al., "Mice Lacking ADPRT and poly(ADP-ribosyl)ation Develop Normally But Are Susceptible to Skin Disease", *Genes Dev.,* 9:509–20 (1995), which is hereby incorporated by reference, ischemic damage can be virtually abolished in neurons with few, if any, undesirable side effects, where PARP inhibition is sufficiently selective.

If PARP activation elicited stroke and neurodegenerative disease damage exclusively through NO, then the neural protection observed in PARP–/– mice, sometimes called "knockout mice", would be no better than that provided by inhibitors of NO or glutamate, a level of protection that has been provided by the well-known, relatively weak non-selective PARP inhibitors. However, it has now been found that "knocking out" the gene for PARP provided substantially greater protection than inhibitors of NO or glutamate. Therefore, the inventors have concluded that other mechanisms, such as oxygen-gree radicals, are surprisingly important in neurotoxicity. Moreover, it has been discovered that these other mechanisms can be eliminated by treatments that selectively and completely, or almost completely, abolish PARP itself. The same result with a drug can be accomplished by the use of a potent, selective PARP inhibitor.

Such an inhibitor would be capable of completely eliminating enzyme activity without undesirable side effects and thereby produce much greater protection against neurotoxicity than is possible with methods previously used.

For example, selective PARP inhibition provides impressive protection against vascular damage in stroke, reducing the infarct volume by as much as 80%, which exceeds the degree of protection reported with known treatments. Maximal protection of 50–65% typically occurs with glutamate receptor antagonists, NOS inhibitors, the immunosuppressant FK506, and non-PARP genetic alterations, such as transgenic nNOS–/– mice and mice overexpressing copper-zinc superoxide dismutase. (Dawson et al., "Resistance to Neurotoxicity in Cortical Cultures from Neuronal Nitric Oxide Synthase Deficient Mice" *J. Neurosci.,* 16:2479–87 (1996); Zhong et al., "Nitric Oxide Activation of Poly(ADP-ribose) Synthetase in Neurotoxicity," *Science,* 263:687–89 (1994); and Chan et al., "Reduced Neurotoxicity in Transgenic Mice Overexpressing Human Copper-zinc-superoxide Dismutase," *Stroke,* 21:11180–2 (1990)). One of the reasons for this superior performance of the more selective PARP inhibitors is that they can be used in sufficiently high doses to completely inhibit PARP activation without incurring potentially serious side effects as a result of interfering with other aspects of metabolism.

Examples of selective PARP inhibitors of the invention include certain benzamide derivatives, phenanthridones, isoquinolines, dihydroisoquinolines, dihydroxyisoquinolines, isoquinolinones, quinazolines, quinazolinones, naphthalimides, hydroxybenzamides, or the pharmacologically acceptable base or acid addition salts thereof, or mixtures thereof. Preferably, the selective inhibitor of the invention is selected from the group consisting of isoquinolines, dihydroisoquinolines, dihydroxyisoquinolines, isoquinazolinones, naphthalamides, and the pharmacologically acceptable base or acid addition salts thereof. Most preferably the selective inhibitor is an isoquinolinone.

Specific examples of useful inhibitors include:
benzoyleneurea,
3-acetamidobenzamide,
3-chlorobenzamide,
3-hydroxybenzamide,
3-methylbenzamide,
3methoxybenzamide,
6-amino-1,2-benzopyrone,
trp-P-1(3-amino-1,4-dimethyl-5H-pyrido[4,3-b]indole),
1-hydroxyisoquinoline,
1,5-dihydroxyisoquinoline,
3,4-dihydro-5-[4-(1-piperidinyl)-butox]-1(2H)-isoquinolinone,
juglone (a natural quinone),
luminol,
1,8-naphthalimide,
4-amino-1,8-naphthalimide,
N-hydroxynaphthalimide sodium salt,
1(2H)-phthalazinone,
phthalhydrazide,
6(5H)-phenanthridinone,
2-nitro-6(5H)-phenanthridinone,
4-hydroxyquinazoline,
2-methyl-4(3H)-quinazolinone,
2-mercapto-4(3H)-quinazolinone,
chlorothenoxazin, and
the pharmacologically acceptable base or acid addition salts thereof.

Most preferably, the selective inhibitor is 3,4-dihydro-5-[4-(1-piperidinyl)-butoxy]-1(2H)-isoquinolinone ("DPQ").

Examples of general groups of non-selective PARP inhibitors include unsaturated long-chain fatty acids. Other families of PARP inhibitors, for example, the benzamides and the quinazolines, may have some specific compounds that are highly selective and some specific compounds that are not particularly selective. Specifically, benzamide and some of its derivatives such as benzoic acid, 3-aminobenzamide and 4-aminobenzamide are recognized as being non-selective, while 3-acetamidobenzamide, 3-chlorobenzamide, 3-hydroxybenzamide, 3-methylbenzamide, 3-methoxybenzamide, may be selective to some degree. Further, while quinazoline itself does not appear to be PARP-selective, the specific derivative 2-methyl-4(3H)-quinozoline does seem to inhibit PARP selectivity over the similar enzyme receptor site for mono (ADP-ribose) transferase.

A convenient method to determine quickly and easily whether a PARP inhibitor compound is selective or non-selective with respect to the PARP receptor site, as opposed to upstream sites for NMDA- or NO-related inhibition, is to treat a cortical cell culture (1) first with the PARP inhibitor being tested to exert a neuroprotective effect, (2) then with an amount of NMDA usually sufficient to induce a neurotoxic condition, (3) then with a selective NOS inhibitor, such as nitroarginine, in an amount usually sufficient to counteract NMDA-induced neurotoxicity, and (4) finally, with a substance that reverses the neuroprotective of the NOS inhibitor such as arginine. If the neuroprotective effect was due to NO-inhibition, upstream of the true PARP receptor site, neurotoxic conditions will return upon the addition of the antagonist to NO-inhibition. On the other hand, if the neuroprotective effect was selective at the point of PARP activation, downstream from NO-production, the neuroprotective effect should persist, even after the addition of the NO-inhibitor antagonist.

A convenient method to determine quickly and easily whether a PARP inhibitor compound is selective or non-selective with respect to the PARP receptor site, as opposed to that of mono(ADP-ribosyl)transferase, is to compare $IC_{50}$ values for the inhibitor being tested for PARP and for another arginine-specific mono(ADP-ribosyl)transferase, for example, from hen heterophils by the procedure of Tanigawa et al., "ADP-ribosyltransferase from Hen Liver Nuclei; Purification and Characterization," *J. Biol. Chem.,* 259:2022–29 (1984) or transferase A from turkey erythrocytes by the procedure of Moss et al., "Isolation and Properties of an NAD- and Guanidine-dependent ADP-ribosyltransferase from Turkey Erythrocytes", *J. Biol. Chem.,* 255:5838–40 (1980). See also, Banasik et al., "Inhibitors and Activators of ADP-ribosylation Reactions", *Molec. and Cell. Biochem.,* 138:185–97 (1994); and Banasik et al., "Specific Inhibitors of Poly(ADP-Ribose) Synthetase and Mono(ADP-ribosyl)transferase", *J. of Biol. Chem.,* 267:1569–75 (1992). The disclosures of these four publications are hereby incorporated by reference into this application.

Appropriate selective PARP inhibitors may be useful in a free base form, in the form of base salts, or in the form of acid addition salts. These three forms are all within the scope of the invention. In practice, the use of a salt amounts to use of the neutral compound. Pharmaceutically acceptable salts within the scope of the invention include those derived from mineral acids, such as hydrochloric acid and sulfuric acid, and those derived from organic acids, such as ethanesulfonic acid, benzenesulfonic acid, p-toluenesulfonic acid, and the like, giving the corresponding hydrochloride, sulfamate, ethanesulfonate, benzenesulfonate, p-toluenesulfonate, and the like, respectively of those derived from the neutral compound.

Examples of suitable inorganic bases for the formation of salts of compounds of the invention include the hydroxides, carbonates, and bicarbonates of ammonia; sodium; lithium; potassium; calcium; magnesium; aluminum; zinc; and the like. Salts may also be formed with suitable organic bases. Organic bases suitable for the formation of pharmaceutically acceptable base addition salts with compounds of the present invention include those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines, such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, "Pharmaceutical Salts," *J. Pharm. Sci.,* 66:1, 1–19 (1977).

The acid addition salts of the basic compounds may be prepared either by dissolving the free base of a selective PARP inhibitor in an aqueous or an aqueous alcohol solution or other suitable solvent containing the appropriate acid or base, and isolating the salt by evaporating the solution. Alternatively, the free base of the selective PARP inhibitor may be reacted with an acid, as well as reacting the PARP inhibitor having an acid group thereon with a base, such that the reactions are in an organic solvent, in which case the salt separates directly or can be obtained by concentrating the solution.

Many of the selective PARP inhibitors are known and, thus, can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly(ADP-ribose) Polymerase", *Anticancer Drug Des.,* 6:107–17 (1991), which discloses for synthesizing a number of different PARP inhibitors. It is understood that tautomeric forms, when possible, are included in the invention.

Typically, selective PARP inhibitors will be more potent than non-selective PARP inhibitors, such as benzamide or 3-benzamide. Specifically, selective PARP inhibitors typically have an $IC_{50}$ for inhibiting poly(ADP-ribose) polymerase in vitro of 33 $\mu$M or lower, preferably 22 $\mu$M or lower and, even more preferably, 40 nM or lower. The selective PARP inhibitor 3,4-dihydro-5-[4-(1-piperidinyl)butox]-1(2H)-isoquinolinone, for example, has been reported to inhibit PARP with an $IC_{50}$ of 40 nM by Suto et al., cited above.

In comparison, non-selective PARP inhibitors, such as benzamide and its derivatives are relatively weak PARP inhibitors with poor bioavailability. At a concentration of 100 $\mu$M, benzamide only provides about a 50% protection against NMDA neurotoxicity. See, for example, Zhang et al. "Nitric Oxide Activation of Poly(ADP-ribose) Synthetase in Neurotoxicity", *Science,* 263:687–89 (1994).

Administration

The administration of a selective PARP inhibitor in the method of the invention may be oral, parenteral (intravenous, subcutaneous, intramuscular, intraspinal, intraperitoneal, and the like), rectal, intraventricular, or any other convenient dosage form. When administered parenterally, the PARP inhibitor will normally be formulated in a unit dosage, injectable from (solution, suspension or emulsion) with a pharmaceutically acceptable vehicle. Such vehicles are preferably non-toxic and non-therapeutic. Examples of such vehicles include water, aqueous solutions, such as saline, Ringer's solution, dextrose solution, and Hanks' solution; and nonaqueous vehicles, such as fixed oils (e.g., corn, cottonseed, peanut, and sesame oil), ethyl oleate, and isopropyl myristate. Sterile saline is a preferred vehicle, and the compounds are often sufficiently water soluble to be made up as a solution for all foreseeable needs. The vehicle may contain minor amounts of additives, such as substances that enhance solubility, isotonicity, and chemical stability, e.g., anti-oxidants, buffers and preservatives.

When administered orally (or rectally), the PARP inhibitors will usually be formulated into a unit dosage form such as a tablet, capsule, suppository or cachet. Such formulations typically include a solid, semisolid, or liquid carrier or diluent. Exemplary diluents and vehicles include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like. The selective PARP inhibitor of the invention is preferably administered as a capsule or tablet containing a single or divided dose of the inhibitor. Preferably, the selective PARP inhibitor is administered as a sterile solution, suspension, or emulsion, in a single or divided dose.

The selective PARP inhibitors are used in amounts that are therapeutically effective. While the effective amount of the PARP inhibitor will depend on the particular inhibitor being used, amounts of the PARP inhibitor varying from about 1% to about 65% have been easily incorporated into liquid or solid delivery systems.

Doses of the components preferably include pharmaceutical dosage units comprising an efficacious quantity of active compound. By an efficacious quantity is meant a quantity sufficient to inhibit PAR and derive the beneficial effects therefrom through administration of one or more of the pharmaceutical dosage units. Preferably, the dose is sufficient to prevent or reduce the effects of vascular stroke or other neurodegenerative diseases. An exemplary daily dosage unit for a vertebrate host comprises an amount of from about 0.001 mg/kg to about 50 mg/kg.

EXAMPLES

Example 1

Attenuation of N-methyl-D-aspartate (NMDA) and NO-toxicity by PARP Inhibitors

Primary cortical cell cultures were prepared from gestational, 16-day fetal mice in a procedure modified from the described in Dawson et al., "Resistance to Neurotoxicity in Cortical Cultures from Neuronal Nitric Oxide Synthase Deficient Mice", *J. Neurosci.*, 16:2479–87 (1996), the disclosure of which is hereby incorporated by reference. Specifically, the cortex was dissected, and the cortical cells were dissociated by a 30-minute digestion in 0.027% trypsin/saline solution (commercially available from Gibco BRL, Gaithersburg, Md.), followed by trituration in modified Eagle's medium (MEM), 20% horse serum, 25 mM glucose and 2 mM L-glutamine.

The cells were plated on 15 mm multi-well plates coated with polyornithine. Four days after plating, the cells were treated with 5-fluoro-2-deoxyuridine for three days to inhibit the proliferation of non-neuronal cells. The cells were then maintained in MEM, 10% horse serum, 25 mM glucose, and 2 mM L-glutamine in an 8% $CO_2$, humidified 37° C. incubator. The growth medium was refreshed twice per week, and the neurons were allowed to mature for 14 days in culture before being used for experiments. Mature levels of nNOS neurons, corresponding to 1–2% of the total neuronal population, were reached by day 14 in culture.

Before treatment, these critical cultures were washed with Tris buffered control salt solution (CSS) containing 120 mM NaCl, 5.4 mM KCl, 1.8 mM $CaCl_2$, 25 mM Tris-HCl (pH 7.4) and 15 mM glucose. The washed cells were treated with NMDA or the NO-donor sodium nitroprusside (SNP) for five minutes and then washed again. The cells were then placed in growth media and returned to the incubator overnight.

Using these cultures, the neuroprotective effects of the selective PARP inhibitor 3,4-dihydro-5-[4-(1-piperidinyl)-butox]-1(2H)-isoquinolinone (DPQ) were compared with the effects of the non-selective PARP inhibitor benzamide (BZD). FIG. 1 shows the PARP inhibitor BZD as triangles and DPQ as circles, as they inhibited toxicity induced by a five-minute exposure to 500 $\mu$M NMDA (open symbols) or 500 $\mu$M sodium nitroprusside (SNP) (closed symbols) in a dose-dependent manner. Each data point represented the mean ± standard error of the mean (SEM) (n=8) of at least two separate experiments and reflected a minimum of 16,000 neurons counted.

These results confirmed that the non-selective inhibitor benzamide provided protection against NMDA- or NO-induced neurotoxicity with an $EC_{50}$ of about 100 $\mu$M. In contrast, DPQ was significantly more potent, providing 50% of maximal protection at 0.2 $\mu$M. At concentrations of 10–100 $\mu$M, DPQ virtually abolished neurotoxicity, while the maximally effective concentration of benzamide only reduced neurotoxicity by 65%. Therefore, the non-selective PARP inhibitor benzamide was 500 times less potent than the selective PARP inhibitor DPQ. Said another way, DPQ was 500 times more potent than benzamide and abolished neurotoxicity at maximal doses.

Significance was determined by a balanced two-way ANOVA demonstrating significance for the effects of DPQ (F=105, $p \leq 0.0001$). The Fisher PLSD post-hoc test difference were determined at $p \leq 0.0001$ when comparing NMDA-treated cultures with NMDA+DPQ or when comparing SNP-treated cultures with SNP+DPQ. A balanced ANOVA demonstrated significance for the effects of benzamide (F=178.42, $p \leq 0.0001$). The Fisher PLSD post-hoc test differences were determined at $p \leq 0.0001$ when comparing NMDA-treated cultures to NMDA+benzamide or when comparing SNP-treated cultures with SNP+benzamide.

These experiments indicated that the selective PARP inhibitor DPQ was more potent that the non-selective PARP inhibitor benzamide with respect to prevention and/or treatment of NMDA-associated neurodegenerative diseases.

Example 2

Reduction of Neurotoxicity in Cerebral Cortical Cultures in PARP–/– Mice

Figure 2A:
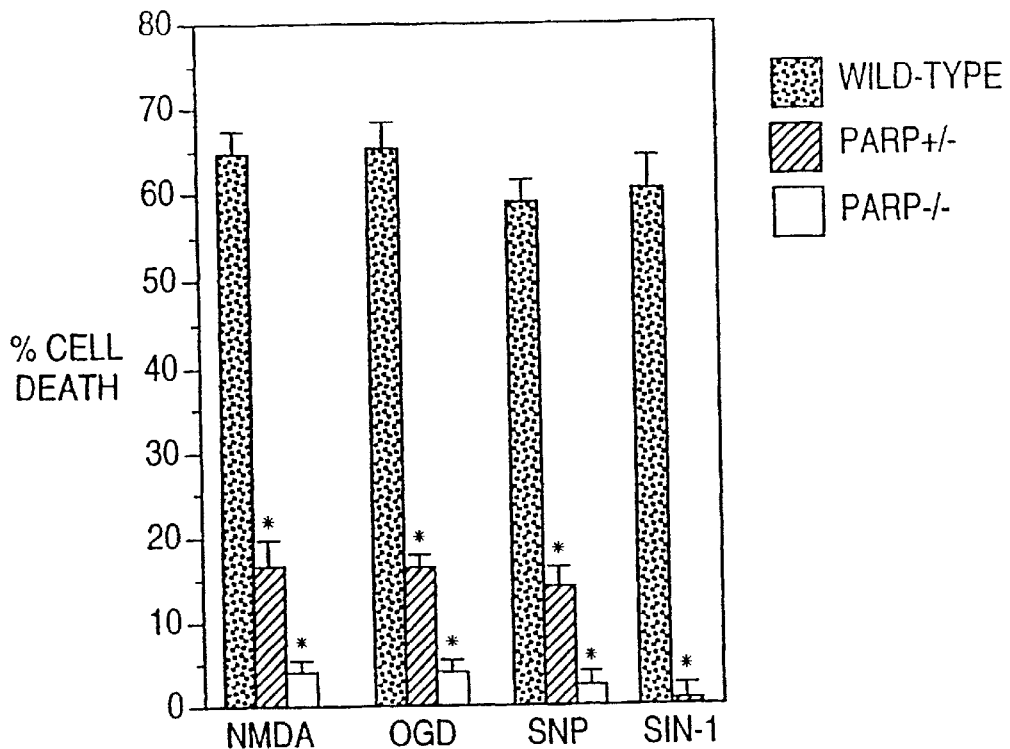
FIG. 2A shows the percentage of cell death when wild-type, PARP+/– and PARP–/– cells are subjected to treatment with the neurotoxic agents NMDA, oxygen-glucose deprivation (OGD), sodium nitroprusside (SNP), and 3-morpholine-sydnonimine hydrochloride (SIN-1).

Mice were obtained having a targeted disruption of the PARP gene (PARP–/–), generated by the method of Wang et al., "Mice Lacking ADPRT and poly(ADP-ribosyl)ation Develop Normally But Are Susceptible to Skin Disease", *Genes Dev.*, 9:509–20 (1995), which is hereby incorporated by reference. The toxicity in cortical cultures elicited by a five-minute exposure to 500 $\mu$M NMDA, by 60 minutes of oxygen and glucose deprivation (OGD), and by NO-donors was evaluated, comparing cultures or cerebral cortical cells from wild-type and PARP–/– mice, as shown in FIG. 2A.

Figure 2B:
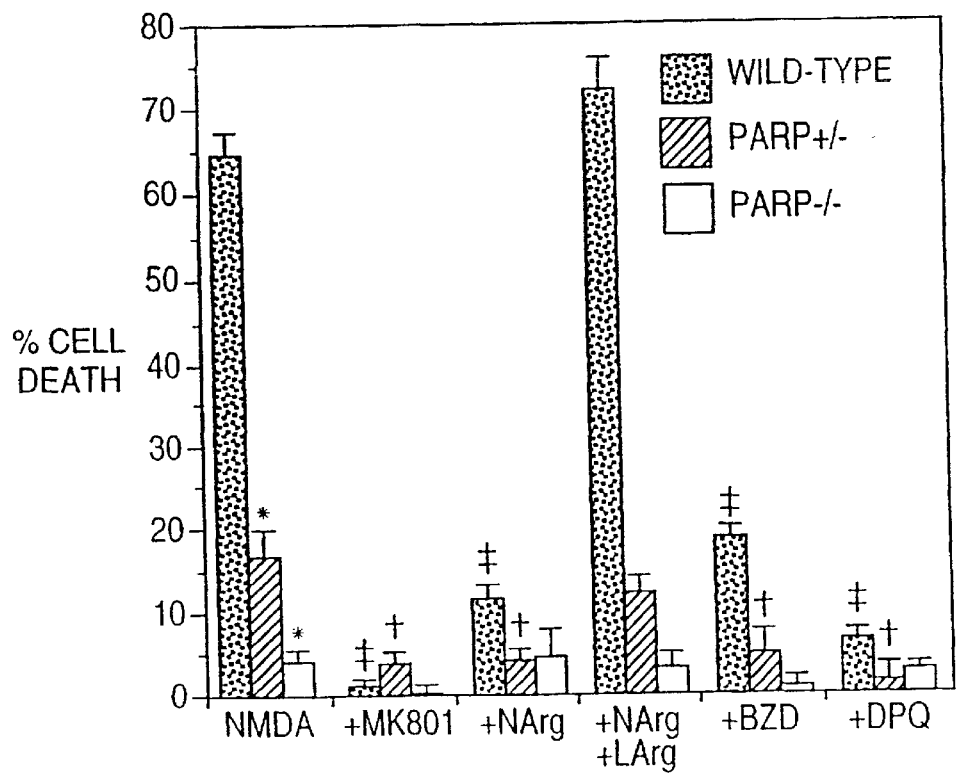
FIG. 2B compares the percentage of cell death when wild-type, PARP+/– and PARP–/– cells, which have been subjected to treatment with NMDA, are further treated with MK801, nitroarginine (NArg), a combination of NArg and L-arginine (LArg), benzamide (BZD) or 3,4-dihydro-5-[4-(1-piperidinyl)-butox]-1(2H)-isoquinolinone (DPQ).

In wild-type cultures, NMDA killed approximately 65% of cells. In cultures from heterozygotes (PARP+/–), toxicity was reduced by 72% (only 17% of the cells were killed). In cultures from PARP–/– animals, however, NMDA-induced neurotoxicity was virtually abolished, with the percentage of cell death not differing significantly from buffer-treated controls. As shown in FIG. 2B, the NMDA antagonist MK801 (1 $\mu$M) abolished NMDA toxicity in wild-type and heterozygote cultures.

Neurotoxicity induced by the NO-donor sodium nitroprusside (SNP)(500 $\mu$M) was reduced by 73% in PARP+/– cultures and completely abolished in PARP–/– cultures. The PARP–/– cultures were also resistant to NO-neurotoxicity induced by another NO-donor, 3-morpholino-sydnonimine hydrochloride (SIN-1)(1 mM). Thus, tissues from homozygous PARP-deleted mice (PARP−/−) displayed a complete loss of PARP catalytic activity and were completely resistant to neurotoxicity, consistent with the downstream position of PARP involvement, relative to NOS activity, in producing neurotoxicity. As a result, neural tissue damage following ischemia and reperfusion injury would have been profoundly reduced in PARP−/− animals.

As NO has been shown to mediate the neurotoxic actions of NMDA, the influence of the NOS inhibitor nitroarginine upon NMDA toxicity was evaluated. Nitroarginine (NArg) (100 $\mu$M), a selective inhibitor of NOS, markedly reduced NMDA toxicity in wild-type cultures and the PARP+/− cultures, as shown in FIG. 2B. However, arginine (L-Arg)(1 mM), which reversed the neuroprotective effect of nitroarginine against NMDA toxicity in wild-type cultures, has no significant effect on PARP−/− cultures.

The influence of a non-selective PARP inhibitor on NMDA neurotoxicity was also examined. Benzamide (BZD) (500 $\mu$M) reduced NMDA toxicity in wild-type cultures and PARP+/− culture, with no significant effect on the negligible residual toxicity of PARP−/− preparation. (FIG. 2B.) In contrast, the selective PARP inhibitor DPQ (10 $\mu$M) produced a significantly greater reduction of NMDA toxicity than benzamide in both wild-type and PARP+/− cultures, with no significant effects on PARP−/− cultures. DPQ also reduced the toxicity elicited by the NO-donor SNP in both wild-type and PARP+/− cultures, with no effect on the PARP−/− cultures. (Not shown in FIG. 2.)

The neurotoxicity in cortical cultures elicited by oxygen-glucose deprivation (OGD) has been shown to involve both NMDA receptor and nNOS activation. See Dawson et al., "Resistance to Neurotoxicity in Cortical Cultures from Neuronal Nitric Oxide Synthase Deficient Mice", *J. Neurosci.*, 16:2479–87 (1996), the disclosure of which is hereby incorporated by reference. Combined OGD was performed as described in Kaku et al., "Antagonism by non-NMDA Receptors Augments the Neuroprotective Effect of NMDA Receptor Blockage in Cortical Cultures Subjected to Prolonged Deprivation of Oxygen and Glucose", *Brain Res.*, 554:344–47 (1991) and/or Monyer et al., "Oxygen or Glucose Deprivation-induced Neuronal Injury in Cortical Cell Cultures is Reduced by Tetanus Toxin, *Neuron*, 8:967–73 (1992), both of which are hereby incorporated by reference.

Specifically, the culture media was completely exchanged with deoxygenated, glucose-free Earle's balanced salt solution (EBSS) containing: 116 mM NaCl, 5.4 mM KCl, 0.8 mM MgSO$_4$, 1 mM NaH$_2$PO$_4$, and 0.9 mM CaCl$_2$, bubbled with 5% H$_2$/85% N$_2$/5% CO$_2$. The cultures were kept in a 37° C., anaerobic chamber for 60 minutes containing the gas mixture 5% H$_2$/85% N$_2$/5% CO$_2$. Combined oxygen-glucose deprivation was terminated by removal of the cultures from the chamber and replacement of the EBSS solution with oxygenated growth media. The cultures were returned to a humidified incubator containing 5% CO$_2$ and atmospheric oxygen at 37° C. overnight.

Toxicity was assayed 20–24 hours after exposure to cytotoxic conditions by microscopic examination with computer-assisted cell counting, following staining of all nuclei with 1 $\mu$g/ml Hoescht 33342 and staining of dead cell nuclei with 7 $\mu$g/ml propidium iodide. All reagents were purchased from Sigma Chemicals, St. Louis, Mo.

Both total and dead cells were counted. Glial nuclei fluoresce at a different intensity than neuronal nuclei and were gated out. The percentage of cell death was determined as the ratio of live to dead cells, as compared to the percentage of cell death in control wells to account for cell death due to mechanical stimulation of the cultures. At least two separate experiments using four separate wells were performed. The results are shown in FIG. 2A, with a minimum of 15,000–20,000 neurons counted per data point, which represented the mean ± standard error of the mean (SEM)(n=8).

In wild-type cortical cultures, 60 minutes of OGD resulted in 65% cell death, which was reduced to 15% in PARP+/− cultures. In PARP−/− cultures, however, OGD toxicity was virtually abolished and was not significantly different from residual toxicity in buffer-treated control cultures. In wild-type cultures and PARP+/− cultures, MK801 (10 $\mu$M) and nitroarginine (NArg)(100 $\mu$M) profoundly reduced toxicity with no differential effects in PARP−/− preparation. L-arginine (1 mM) again reversed the nitroarginine protection of cultures in wild-type and PARP+/− culture preparations, but not in PARP−/− cultures. Benzamide (500 $\mu$M) reduced OGD toxicity in wild-type and PARP+/− culture preparations to the same extent that it diminished NMDA toxicity, with no influence upon PARP−/− preparations. DPQ (10 $\mu$M) also abolished OGD toxicity for wild-type and PARP+/− culture, as it did for NMDA toxicity. These observations also confirmed the primary role of PARP itself in NMDA-mediated neurotoxicty.

Significance was determined by a balanced two-way ANOVA, demonstrating significance for the effects of NMDA exposure on genotype (F=96.359, p$\leq$0.0001) or treatment (F=18.931, p$\leq$0.0001). Significance was demonstrated for the effects of OGD exposure on genotype (F=406, p$\leq$0.0001) or treatment (F=191, p$\leq$0.0001). The Fisher PLSD post-hoc test demonstrated differences at p$\leq$0.0001) when comparing wild-type NMDA-, SNP-, or SIN-1 or OGD-treated wild-type cultures with PARP+/− and PARP−/− cultures (genotype). The Fisher PLSD post-hoc test demonstrated differences at p$\leq$0.0001 when comparing wild-type NMDA- or OGD-treated cultures to cultures with the addition of MK801, NArg, BZD or DPQ, and differences at p$\leq$0.0001 when comparing NMDA-treated cultures from PARP+/− to MK801, NArg, BZD or DPQ treatments in the PARP+/− cultures (treatment).

These results indicated that specific genetic disruption of the PARP allele provided profound protection against glutamate-NO mediated ischemic insults in vitro.

Example 3

Protection against Focal Ischemia in PARP-deficient Mice

Oxygen-glucose deprivation and NMDA-neurotoxicity in primary neuronal cultures, an in vitro model commonly used to study early mechanisms of vascular stroke damage, was used to evaluate the extent of brain injury following middle cerebral artery occlusion (MCAo) in transgenic PARP+/− and PARP−/− mice, as compared with wild-type mice (129/SV, a strain of related 129 mice).

Figure 4:
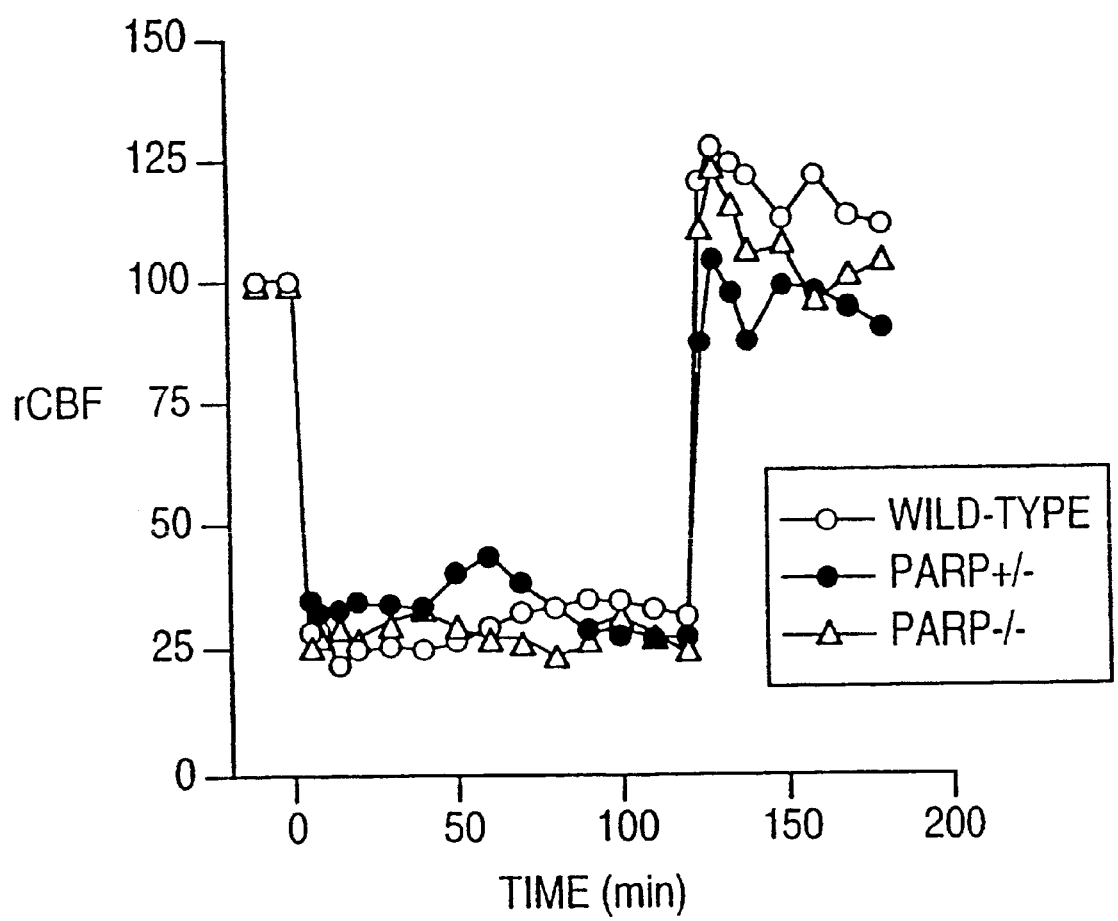
FIG. 4 shows the regional cerebral blood flow before, during, and after two hours of middle cerebral artery occlusion in wild-type, PARP+/– and PARP–/– mice.
Figure 5:
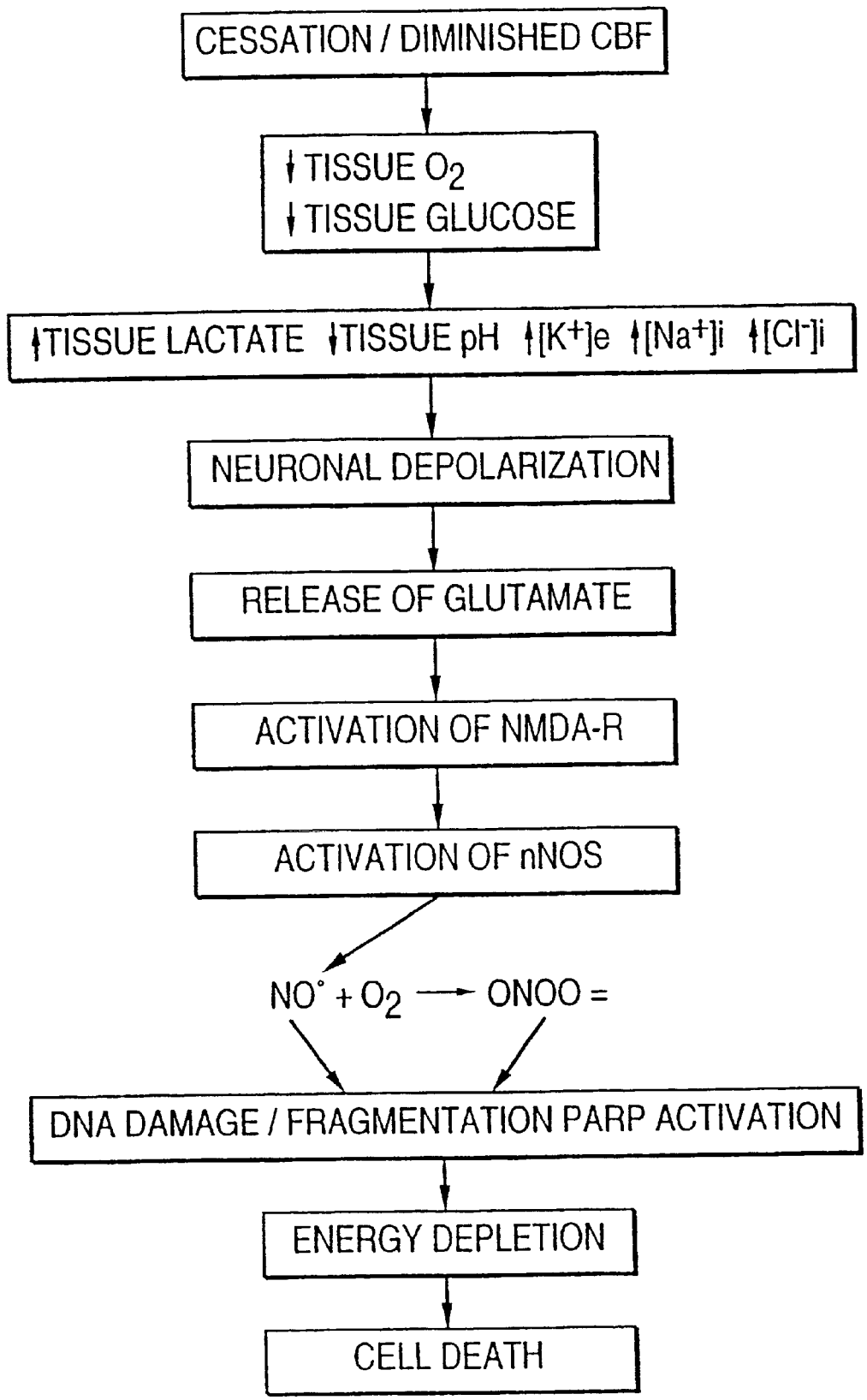
FIG. 5 shows a simple model of PARP activation in ischemia.

The study was conducted in accordance with NIH guidelines for the use of experimental animals, and the protocols were approved by the Institutional Animal Care and Use Committee. The three groups of mice were subjected to two hours of MCAo, in which regional cerebral blood flow (rCBF) was decreased to approximately 30% of baseline, as shown in FIG. 4.

Specifically, ten adult male, 129/SV mice (Taconic Farms) or mutant PARP mice (four wild-type; four PARP+/−; and four PARP−/−) weighing 23–38 g were anesthetized with 1–1.2% halothane in oxygen-enriched air by face mask. To monitor rCBF before, during and after two hours of middle cerebral artery occlusion, a laser-doppler probe was placed on the skull ipsilateral to the occlusion: 2 mm posterior and 3 mm lateral from the bregma. The data for FIG. 4 were analyzed by a one-way ANOVA with Fisher's post-hoc test. There were no significant differences between the groups. The standard deviations are not shown in FIG. 4 for the sake of clarity, but the mean of the standard deviation for each data point was 8.2.

The femoral arteries of the anesthetized mice were cannulated for measurement of arterial-blood gases and blood pressure. Rectal temperature was controlled at near 37° C. throughout the experiment with heating lamps/water pads in all animals.

After baseline arterial blood gas measurements, unilateral MCA occlusion was performed by inserting a 5-0 nylon monofilament into the intraluminal space of the external carotid artery. The filament was introduced into the internal carotid artery via the external carotid artery up to a point 6-mm distal to the internal carotid artery-pterygopalatine artery bifurcation. Concurrently, the ipsilateral common carotid artery was occluded by a temporary clip. After two hours of ischemia, the test animals were briefly re-anesthetized with halothane, and the filament was withdrawn through the external carotide artery, allowing reperfusion of the common and internal carotid arteries, but not the external carotid artery. After removal of the filament, rCBF immediately increased to 90–110% of the baseline value.

This was followed by 22 hours of reperfusion, after which the extent of infarct was determined by harvesting the brains of the test animals. The forebrain was sliced into five coronal sections, two mm thick each. These sections were stained with 1% 2,3,5-triphenyltetrazolium chloride, as described by Bederson et al., "Evaluation of 2,3,5-triphenyltetrazolim Chloride as a Stain for Detection and Quantification of Experimental Cerebral Infarction in Rats", *Stroke*, 17:1304–1308 (1996), the disclosure of which is hereby incorporated by reference. Infarct volume was determined by numeric integration of areas of distinct pallor with cross-sectional thickness using digital planimetry.

Figure 3A:
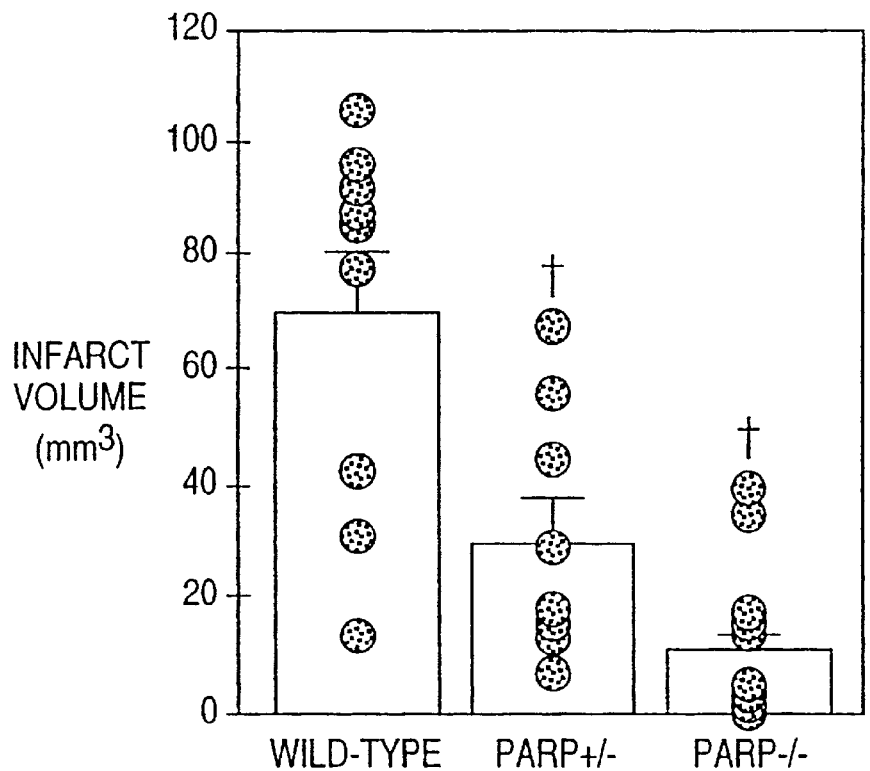
FIG. 3A shows the infarct volume of forebrains after transient focal ischemia in wild-type, PARP+/– and PARP–/– mice.

The results are graphically depicted in FIG. 3A, with transient focal ischemia in wild-type test animals being indicated by open circles, in PARP+/− mice indicated by closed circles, and in PARP−/− mice indicated by open triangles. As shown in FIG. 3A, infarct volume was reduced from 69.0 mm³ to 15.4 mm³ (about 80%) in PARP−/− mice when compared with wild-type animals. Infarct volume in PARP+/− animals was also reduced from 79.0 mm³ to 30.1 mm³ (about 65%) when compared to wild-type animals. These data are presented as the mean ± SEM (Control, n=9; PARP+/−, n=8; PARP−/−, n=8). Additionally, data from each individual animal was plotted as a separate point overlaid on each histogram bar.

In two of the PARP−/− animals, negligible infarct volume was observed, and three animals displayed no neurologic deficit after 22 hours of reperfusion. These particular animals were apparently completely protected against stroke damage. However, because it was possible that the filament may not have been optimally placed in these two animals to elicit MCAo, data from these two were not included in the analyses of infarct volume shown in FIG. 3A. If data from these two mice had been included, the overall infarct volume for the PARP−/− group would have been decreased from 15.4±1.8 mm³ to 12.1±1.6 mm³ (n=10).

Figure 3B:
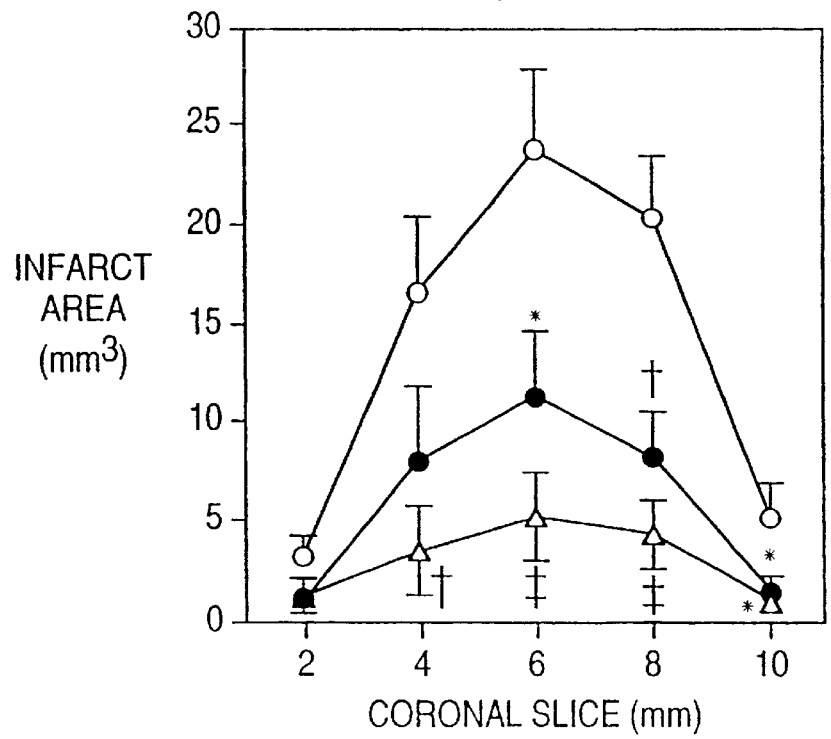
FIG. 3B shows the infarct area in coronal slices of forebrains after transient focal ischemia in wild-type, PARP+/– and PARP–/– mice.

Further, significant decreases in injury were evident in each of the five coronal sections except in the most anterior two mm, as shown in FIG. 3B. Significant protection also occurred in the three most caudal sections for PARP+/− mice.

Significance was determined by comparing PARP+/− or PARP−/− to wild-type by a one-way ANOVA with Fisher's post-hoc test ($p \leq 0.05$, 0.01 and 0.001 respectively).

Because hemodynamic alterations can markedly influence the effects of vascular stroke, various physiological indications were monitored in wild-type (129/SV), PARP+/− and PARP−/− animals before, during and after MCAo under halothane anesthesia, as shown below in Table 1.

| Parameters | Animal | Before* | During* | After* |
|---|---|---|---|---|
| MABP[1] | Wild Type[2] | 86 ± 4[5] | 85 ± 5 | 79 ± 5 |
| | PARP +/−[3] | 89 ± 9 | 86 ± 9 | 76 ± 4 |
| | PARP −/−[4] | 81 ± 8 | 81 ± 5 | 78 ± 6 |
| Core Temperature (° C.) | Wild Type | 35.7 ± 5 | 35.9 ± 0.4 | 35.7 ± 0.5 |
| | PARP +/− | 35.7 ± 0.5 | 36.0 ± 0.6 | 35.9 ± 0.6 |
| | PARP −/− | 36.0 ± 0.4 | 36.2 ± 0.4 | 36.1 ± 0.8 |
| Arterial pH | Wild Type | 7.27 ± 0.02 | 7.27 ± 0.02 | |
| | PARP +/− | 7.28 ± 0.01 | 7.28 ± 0.00 | |
| | PARP −/− | 7.27 ± 0.02 | 7.27 ± 0.01 | |
| Arterial PaCO$_2$ | Wild Type | 41 ± 8 | 40 ± 1 | |
| | PARP +/− | 37 ± 3 | 39 ± 3 | |
| | PARP −/− | 38 ± 3 | 38 ± 1 | |
| Arterial PaO$_2$ | Wild Type | 145 ± 12 | 136 ± 10 | |
| | PARP +/− | 141 ± 8 | 120 ± 20 | |
| | PARP −/− | 126 ± 34 | 116 ± 22 | |

*"Before" means before occlusion; "During" means during the two-hour ischemia period; and "After" means during a period of up to 30 minutes after reperfusion. All values were averaged over 15 minutes for the "before" period, over two hours for the "during" period, and over one hour "after" middle cerebral artery occlusion.
[1]"MAPB" is the mean arterial blood pressure in the millimeters of mercury.
[2]For wild type, n = 4.
[3]For PARS +/−, n = 3.
[4]For PARS −/−, n = 3.
[5]Data are presented as the mean ± the standard deviation of the mean.

There were no significant differences in mean arterial blood pressure, core temperature, or blood gases between the groups that could provide non-specific neuroprotection. Thus, the reduction of infarct volume in the PARP+/− and PARP−/− animals did not result from altered hemodynamic effects on cerebral blood flow, body temperature, blood gases or blood pressure.

These experiments indicated that a PARP inhibitor that was selective for the actual PARP receptor site, such as DPQ, would be significantly more effective with respect to prevention and/or treatment of vascular stroke, than a non-selective PARP inhibitor, which has the effect of inhibiting PARP primarily by NMDA- and/or NO-inhibition at a point relatively upstream of actual PARP activation and, thus, would likely have a number of different physiological side effects. This is true because vascular stroke represents a complex pattern of pathology that is believed to be caused by any number of different factors, only some of which are known to be NMDA- and NO-associated.

Example 4

Reduced PARP Expression and Catalytic Activity in PARP-deficient Mice

Because of the pronounced reduction in neurotoxicity and stroke damage in PARP+/− as well as PARP−/− mice, PARP protein expression and catalytic activity in the adult mouse forebrain were compared with that of wild-type mice.

Protein expression was determined by Western blot analysis, as follows: Fresh mouse brain was homogenized in 20% (w/v) 50 mM Tris-HCl (pH 7.4) buffer containing 1 mM EDTA, 1 mM dithiothreitol, 50 mM NaCl, 0.25 M sucrose, 0.2 mM PMSF, and 1 mg/ml of chymostatin, leupeptin, and pepstatin. The homogenate was centrifuged at 1000 g for 15 minutes at 4° C. The pellet, which contained the nuclear fraction, was then washed with the homogenizing buffer. The nuclear fraction was dissolved in SDS-PAGE sample buffer containing 4 M urea. The mixture was subjected to extensive sonication, followed by boiling at 90° C. for 15 minutes. The PARP protein (200 $\mu$g) was separated on a gradient SDS-PAGE and identified by anti-PARP monoclonal antibody by the electron capture luminescence (ECL) method.

For the PARP catalytic assay, PARP activity was assessed using a self-modification assay method previously described by Zhang et al., "Nitric Oxide Activation of Poly(ADP-ribose) Synthetase in Neurotoxicity", *Science,* 263:687–89 (1994), the disclosure of which is hereby incorporated by reference. Fresh mouse brain tissues were homogenized in 20% (w/v) 50 mM Tris-Cl (pH 7.4) buffer containing 1 mM EDTA, 1 mM dithiothreitol, 50 mM NaCl, 0.25 M sucrose, 0.2 mM PMSF, and 1 $\mu$g/ml of chymostatin, leupeptin and pepstatin. The homogenate was centrifuged at 100 g for 15 minutes at 4° C. The nuclear fraction, referred to as the pellet, was then washed with the homogenizing buffer. The washed pellet was re-suspended in the homogenizing buffer. In a typical PARP assay, each 50 $\mu$l mixture contained 0.1 mM [adenylate-$^{32}$P]NAD (10 Ci/mmol) (NEN, Life Sciences, Boston, Mass.).

Following a five-minute incubation at 25° C. 25 $\mu$l of 50% ice-cold TCA was added to each mixture. The mixture was centrifuged at 8,000 g for 5 minutes. The resulting pellet was subjected to two more washes of 50% TCA and two washes of ice-cold acetone. After a brief air-drying, the pellet was dissolved in SDS-PAGE sample buffer containing 4 M urea and was boiled at 90° C. for 15 minutes. The PARP was separated on 8% SDS-PAGE. The gel was fixed, dried, and exposed to a phosphoimager cassette. In the wild-type catalytic assay, other ribosylated nuclear proteins were seen as a gray background, which was reduced with benzamide treatment and was absent in the PARP+/– and PARP–/– lanes, confirming the reduced expression and absence of PARP protein in the brains of these animals.

As a result of the experiment, PARP protein and catalytic activity were detected at modest levels in wild-type mouse forebrain. PARP protein expression was markedly reduced from wild-type in the PARP+/– forebrain and was not detectable at all in the PARP–/– forebrain. PARP catalytic activity was not detectable in the forebrains from either PARP+/– or PARP–/– mice.

Because the PARP assays used could have detected as little as 20% of wild-type activity, the enzyme activity was probably reduced by at least 80% in the PARP+/– mice, despite a lesser depletion of PARP protein. The marked reduction in PARP expression in PARP+/– mice may suggest that more than gene copy number affected the expression of PARP in the adult brain. Since PARP is involved in regulating the normal activity of numerous nuclear proteins, it is possible that the loss of a single PARP allele significantly affected the transcriptional elements that regulate the mature expression of PARP, resulting in lower than expected protein expression.

Example 5

Absence of ADP-Ribose Polymer Formation in PARP–/– Cortex Following Infarction

The relative amounts of ADP-ribose polymer formation were examined as a marker of PARP catalytic activity. Following two hours of ischemia by MCAo and two hours of reperfusion, the brains of the test animals were rapidly removed and flash frozen. To detect poly(ADP-ribose) synthase activation, 15 $\mu$m thick sections from the freshly frozen brains were incubated in 200 $\mu$M NAD at 37° C. for 45 minutes with modifications from the procedure taught by Kupper et al., "Detection of Poly(ADP-ribose) Polymerase and its Reaction Product Poly(ADP-ribose) by Immunocytochemistry", *Histochem. J.,* 28:391–95 (1996), the disclosure of which is hereby incorporated by reference.

Specifically, sections were fixed in 95% ethanol at –20° C. for ten minutes and incubated overnight with mouse anti-poly(ADP-ribose) monoclonal antibody (available from BIOMOL Research Laboratories, Plymouth Meeting, Pa.) at a 1:100 dilution. A biotin-SP-conjugated goat anti-mouse IgG, F(ab')$_2$ specific antibody (obtained from Jackson ImmunoResearch Laboratories, West Grove, Pa.) was used as secondary at a 1:100 dilution. For signal amplification, an immumoperoxidase ABC kit (Vector Laboratories, Burlingame, Calif.) was used, followed by a TSA-Indirect kit (NEN Life Sciences, Boston, Mass.). Diaminobenzidine was used as a chromogen (Gibco BRL, Gaithersburg, Md.).

The ipsilateral cortex of wild-type mice expressed high levels of nuclear ADP-ribose polymer formation as identified by immunohistochemistry, but there was minimal nuclear staining in the contralateral hemisphere of the same animal. In contrast, following the same two hours of MCAo and two hours of reperfusion in the PARP–/– animals, there was a complete absence of any ADP-ribose polymer staining in either the ipsilateral or the contralateral cortical hemisphere.

Contrast in photomicrographs taken of PARP–/– tissue was adjusted to allow visualization of tissue in the complete absence of staining. Photomicrographs were taken with a 630X objective on a cooled CCD camera. The resulting images were consistent with duplicate experiments using either a monoclonal antibody or polyclonal antibodies.

The invention being thus described, it will be obvious that the same may be varied in many ways. Such variations are not to be regarded as a departure from the spirit and scope of the invention, and all such modifications are intended to be included within the scope of the following claims.

We claim:

1. A method of preventing neural tissue damage resulting from ischemia and reperfusion injury or neurodegenerative diseases in a mammal comprising administering to a mammal a therapeutically effective amount of 3,4-dihydro-5-[4-(1-piperidinyl)-butox]-1 (2H)-isoquinolinone, a selective inhibitor of poly(ADP-ribose) polymerase.

2. The method of claim 1 wherein said selective inhibitor is administered intravenously, intraperitoneally, intramuscularly, intraventricularly, or orally.

3. The method of claim 1 wherein said selective inhibitor is administered as a capsule or tablet containing a single or divided dose of said inhibitor, wherein said dose is sufficient to prevent or reduce the effects of vascular stroke or other neurodegenerative disease.

4. The method of claim 1 wherein said selective inhibitor is administered as a sterile solution, suspension, or emulsion, in a single or divided dose.

5. A method of preventing neural tissue damage resulting from ischemia and reperfusion injury or neurodegenerative diseases in a mammal comprising administering to a mammal a therapeutically effective amount of a selective inhibitor of poly(ADP-ribose) polymerase, wherein said selective inhibitor is selected from the group consisting of 6(5H)-phenanthridinone, 2-nitro-6(5H)-phenanthridinone, and pharmacologically acceptable base or acid addition salts thereof.

6. A method of preventing neural tissue damage resulting from ischemia and reperfusion injury or neurodegenerative diseases in a mammal comprising administering to a mammal a therapeutically effective amount of a selective inhibitor of poly(ADP-ribose) polymerase, wherein said selective inhibitor is selected from the group consisting of 4-hydroxyquinazoline, 2-methyl-4(3H)-quinazoline, 2-mercapto-4(3H)-quinazoline, and pharmacologically acceptable base or acid addition salts thereof.

7. A method of preventing neural tissue damage resulting from ischemia and reperfusion injury or neurodegenerative diseases in a mammal comprising administering to a mammal a therapeutically effective amount of a selective inhibitor of poly(ADP-ribose) polymerase, wherein said selective inhibitor is selected from the group consisting of benzoyleneurea, 6-amino-1,2-benzopyrone, trp-P-1(3-amino-1,4-dimethyl-5H-pyrido[4,3-b]indole), juglone, luminol, 1(2H)-phthalazinone, phthalhydrazide, chlorothenoxazin, and pharmacologically acceptable base or acid addition salts thereof.

* * * * *

UNITED STATES PATENT AND TRADEMARK OFFICE
CERTIFICATE OF CORRECTION

PATENT NO. : 6,358,975 B1
DATED : March 19, 2002
INVENTOR(S) : Mikael Eliasson et al.

It is certified that error appears in the above-identified patent and that said Letters Patent is hereby corrected as shown below:

<u>Title page,</u>
Item [75], Inventors, -- Roscindale, MA -- has been inserted after
"Mikael J. Eliasson".

Signed and Sealed this

Thirty-first Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,358,975 B1
DATED : March 19, 2002
INVENTOR(S) : Mikael Eliasson et al.

It is certified that error appears in the above-identified patent and that said Letters Patent is hereby corrected as shown below:

<u>Column 1,</u>
Lines 1-5, -- This invention was made using funds from the U.S. government under grant(s) from the National Institute of Health numbered NS01578, NS33277, NS33668, NS20020, NS09951, MH18501; and DA00074. The U.S. government therefore retains certain rights in the invention. -- has been added after the title.

Signed and Sealed this

Twenty-seventh Day of January, 2004

JON W. DUDAS
*Acting Director of the United States Patent and Trademark Office*